United States Patent [19]

Balganesh et al.

[11] Patent Number: 5,399,490
[45] Date of Patent: Mar. 21, 1995

[54] VECTOR TO PRODUCE BIOLOGICALLY IMPORTANT PEPTIDES

[75] Inventors: Tanjore S. Balganesh; Goutam Das; Sandhya S. Visweswariah, all of Bangalore, India

[73] Assignee: Aktiebolaget Astra, Sweden

[21] Appl. No.: 715,941

[22] Filed: Jun. 14, 1991

Related U.S. Application Data

[63] Continuation-in-part of Ser. No. 538,927, Jun. 15, 1990, abandoned.

[51] Int. Cl.⁶ ................ C12N 15/17; C12N 15/16; C12N 15/70; C12N 15/63
[52] U.S. Cl. .................... 435/69.8; 435/69.4; 435/320.1; 435/252.8; 536/24.1; 935/47; 935/48
[58] Field of Search ............. 435/69.4, 69.8, 172.1, 435/172.3, 320.1, 252.8, 849; 530/303, 316; 536/27, 23.1, 23.51, 24.1; 935/47, 48, 55

[56] References Cited

U.S. PATENT DOCUMENTS

4,772,684  9/1988  Brunck ................. 530/316
4,963,495  10/1990  Chang ................. 435/320.1

OTHER PUBLICATIONS

Guzman-Verduzco et al., *Infection & Immunity* 57(2):645–648 (1989).
Okamoto, K. et al. *J. of Bacteriology* 172(9):5260–5265 (1990).
Dwarakanath, P. et al., *Gene* 81:219–226 (1989).
So, M. et al. *PNAS* 77(7):4011–4015 (1980).
Stieglitz, H. et al., *Plasmid* 20:42–53 (1988).
Suggs, S. et al. "Use of Synthetic Oligonucleotides as Hybridization Probes." *PNAS* 78(11)6613–6617 (1981).
Marston, F. A. O. "The Purification of Eukaryotic Polypeptides Synthesized in *E. coli.*" *Biochem J.* 240:1–12 (1986).

*Primary Examiner*—Robert A. Wax
*Assistant Examiner*—Dian C. Jacobson
*Attorney, Agent, or Firm*—White & Case

[57] ABSTRACT

In this patent application we have described the construction of a novel secretion vector based on *E. coli* enterotoxin coding sequence. We have shown categorically that pre and pro regions of toxin gene are absolutely necessary for extra cellular secretion of the stable toxin. We have also shown with specific examples that when the nucleotide coding sequence of a heterologous peptide is fused in frame to the end of the pro region in the st gene, the resultant vector in an *E. coli* host secretes extracellularly correctly processed heterologous peptide. This application also includes construction of suitable vectors where this gene fusion can be achieved. Generally methods to create such fusions involving a) recombinant DNA technology and b) the use of site directed in vitro mutagenesis, have also been described. A general method of purification of heterologous peptides is also described in this application. This novel vector system can be used for hyperproduction and extracellular secretion of peptides of biological importance.

30 Claims, 6 Drawing Sheets taattactatgtcttcgtacggggagagtatagtatga tgttcaccacaaaataaaagttccgccaattgttctgg tttgattcaaatgttcgtggatgccatgccatgttccggaggt aat ATG AAG AAA TCA ATA TTA TTT ATT TTT CTT TCT GTA TTG TCT TTT TCA CCT TTC
    Met Lys Lys Ser Ile Leu Phe Ile Phe Leu Ser Val Leu Ser Phe Ser Pro Phe
Pro
CCT
GCT CAG GAT GCT AAA CCA GTA GAG TCT TCA AAA GAA AAA ATC ACA CTA GAA TCA AAA AAA
Ala Gln Asp Ala Lys Pro Val Glu Ser Ser Lys Glu Lys Ile Thr Leu Glu Ser Lys Lys TGT AAC ATT GCA AAA AAA AGT AAT AAA AGT GGT CCT GAA AGC ATG AAT AGT AGC AAT TAC
Cys Asn Ile Ala Lys Lys Ser Asn Lys Ser Gly Pro Glu Ser Met Asn Ser Ser Asn Tyr TGC TGT GAA TTG TGT TGT AAT CCT GCT TGT ACC GGG TGC TAT TAA taatataaa
Cys Cys Glu Leu Cys Cys Asn Pro Ala Cys Thr Gly Cys Tyr  ...

gggactaaacagtcccttatatttgttcctgattctg atgatgtctgtaacgtatgtacctgtttgctttgttgaat aaatcga

*Fig. 1.*

PURIFICATION OF ST (N54→H54) PEPTIDE

VECTOR TO PRODUCE BIOLOGICALLY IMPORTANT PEPTIDES

This application is a continuation-in-part of application Ser. No. 07/538,927, filed Jun. 15, 1990, now abandoned.

FIELD OF THE INVENTION

In this patent application we have described the construction of a novel secretion vector based on *E. coli* enterotoxin coding sequence. We have shown categorically that pre and pro regions of toxin gene are absolutely necessary for extra cellular section of the stable toxin. We have also shown with specific examples that when the nucleotide coding sequence of a heterologous peptide is fused in frame to the end of the pro region in the st gene, the resultant vector in an *E. coli* host secretes extracellularly correctly processed heterologous peptide. This application also includes construction of suitable vectors where this gene fusion can be achieved. General methods to create such fusions involving a) recombinant DNA technology and b) the use of site directed in vitro mutagenesis, have also been described. A general method of purification of heterologous peptides is also described in this application. This novel vector system can be used for hyperproduction and extracellular secretion of peptides of biological importance.

BACKGROUND OF THE INVENTION AND PRIOR ART

Secretory as well as many membrane proteins are initially synthesized as nascent intracellular preproteins with a signal peptide attached to the N-terminus. The signal peptide enables the protein to cross the inner membrane barrier. In this process the protein gets cleaved and released as a mature protein which normally resides in the periplasmic space. Some exceptions to this mechanism are certain membrane proteins whose signal peptides remain uncleaved (S. Letenhardt, et al. in Protein Engineering, Application in Science, Medicine and Industry edt. by M, Inouye and R. Sharma, 1986 Academic Press, Inc., 157-171). A few prokaryotic proteins or peptides are synthesized as large precursors possessing signal peptides (pre-region) as well as pro-regions. Both segments are cleaved to yield mature proteins or peptides. Examples include subtilin of *Bacillus subtilis* (C. Nishio, et al, 1983, Biochem. Biophys. Res. Commun. 116, 751-758) or stable toxin of *Escherichia coli* (P. Dwarakanath, et al, 1989, Gene 81, 219-226). Enterotoxigenic *E. coli* (ETEC) strains cause diarrhoea in humans by the elaboration of extra cellular toxins classified as heat labile (LT) and heat stable (ST) family of toxins (R. N. Greenberg and R. L. Guerrant (1981). Pharmacol. Ther. II, 507-537; M. D. Gill and M. Woolkalis 1985 in Microbial toxins and diarrhoeal diseses, Ciba Foundation symposium 112, Pitman, London, 57-73). ST toxins are of two types: methanol soluble toxins (STI) and methanol insoluble toxins (STII). STI is further classified into 3 groups depending upon the origin i.e. STh (human), STp (porcine) and STb (bovine). The genes for both the LT and ST are plasmid encoded. The nucleotide sequence of the st gene is shown in FIG. 1. (P. Dwarakanath et al, 1989, Gene 81, 219-226). From the nucleotide sequence as well as from the translated amino acid sequence it is concluded that the 72 amino acid peptide is a precursor of ST which is processed post translationally to release 19 amino acid peptide from the carboxy terminal as the biologically active toxin. (P. Dwarakanath et al, 1989, Gene, 81, 219-226).

Attempts have been made by many groups to utilize the "signal sequence" portion of naturally occuring secretory proteins to construct recombinant vectors that will secrete heterologous proteins. In many cases synthetic signal sequences are also used. In all these cases the recombinant products are localized within the subcellular compartments. Specific examples are: A patent by Gray et al (U.S. Pat. No. 4,755,465 Jul. 5, 1988) where the inventors have claimed that they have constructed a vector which promotes the secretion of correctly processed human growth hormone (hGH) in *E. coli* and Pseudomonas. The "signal sequence" which also comes under the patent claim is very different from *E. coli* stable toxin "signal sequence".

II. A second patent (U.S. Pat. No. 4,704,362 dated Nov. 3, 1987) by Itakura et al. describes a recombinant cloning vehicle for microbial polypeptide expression where a fusion product of β-gal and somatostatin is produced and then processed in vitro to get the final product.

An example where specifically an enterotoxin signal sequence is employed, is by Gray et al. (U.S. Pat. No. 4,680,262, 1985) where the inventors linked methanol insoluble stable toxin (STII) "signal sequence" with human growth hormone (hGH) gene and localized the product in the periplasmic region of the host cell. It is interesting to note that inventors were specifically looking for an expression vehicle which localized the expressed recombinant protein intracellularly. The st II signal sequence bears no similarity to the st I signal sequence and therefore it is considered a different structure.

In this patent application the inventors have taken advantage of both the pre and the pro region of STI to create a recombinant vehicle in which the nucleotide sequence coding for a peptide is fused inframe at the terminus of the pro region. Expression of the whole gene, resulted in the secretion of the recombinant peptide extracellularly and it was correctly processed. A schematic diagram of the principle is shown below:

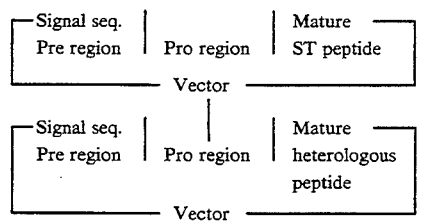

The advantage of this system is that the purification of the recombinant product becomes much simpler as the cells harboring such a recombinant vector can be grown in a synthetic medium and therefore the secreted peptide constitutes the major peptide present in the culture supernatant. A general method of purification of such a recombinant heterologous peptide (AngiotensinI) is described here.

SUMMARY

Utilizing the pre and the pro region of *E. coli* st I gene of the human variety a novel recombinant vector has been constructed which can properly process and extracellularly secrete any peptide. This process is achieved by fusing a coding sequence to the terminus of the pro region. A generalized method of purification of such a recombinant peptide, is described in this application.

The present invention is summarized as follows in the following clauses:

1. The use of E. coli st pre-pro sequence coding for (single letter code) M K K S I L M I F L S V L S F S P F A Q D A K P V E S S K E K I T K E S K K C N I A K K S N K S G P E S M in the development of a vector for secretion of heterologous proteins.

2. The vector pARC 0101, deposit no. NCIB 40115.

3. An E. coli host containing the vector pARC 0101 according to clause 2.

4. The use of pARC 0101 according to clause 2 in the construction of an expression vector for heterologous proteins.

5. A vector containing the E. coli st pre-pro sequence as defined in clause 1.

6. A vector according to clause 5, containing the Bam HI-Hind III sequence of the E. coli st pre-pro sequence as defined in clause 1.

7. A E. coli host containing a vector as defined in any of clauses 5 and 6.

8. A process for the production of heterologous proteins in E. coli, by growing, by standard methods, an E. coli host as defined in clause 7 and isolating, by standard methods, the desired protein product.

9. A process according to clause 8 wherein the protein product is secreted extra-cellularly.

10. The construct pARC 0726 containing the E. coli st pre-pro sequence fused with the Angiotensin I coding sequence in frame.

11. The use of the construct pARC 0726 according to clause 11 in the expression of Angiotensin I.

12. An E. coli host containing the construct pARC 0726 according to clause 10.

13. A process for the production of Angiotensin I by growing an E. coli host according to claim 12 and isolating the desired protein product.

14. A process according to clause 13 wherein the protein product is secreted extra-cellularly.

15. The construct pARC 0801 containing an internal Eco RI site, said Eco RI site having been created by using the alternate codon for Ser 55 of the mature ST peptide.

16. The use of a first construct pARC 0801 according to clause 15 as a starting material in the preparation of a second construct by fusion of a heterologous or homologous gene sequence at the Eco RI site of the pARC 0801 construct.

17. A vector, capable of facilitating the secretion of heterologous protein expressed in a host cell, said vector including DNA encoding the E. coli st pre-pro sequence M K K S I L M I F L S V L S F S P F A Q D A K P V E S S K E K I T K E S K K C N I A K K S N K S G P E S M.

18. A construct comprising a vector according to clauses 5, 6 or 17, fused in reading frame to DNA encoding a desired protein.

19. A construct according to clause 18 wherein the DNA encodes Angiotensin I.

20. A construct according to clause 18 wherein the DNA encodes insulin A chain.

21. A construct according to clause 18 wherein the DNA encodes insulin B chain.

22. The construct pARC 0726 containing the E. coli st pre-pro sequence fused with the insulin chain A coding sequence in frame.

23. The construct pARC 0726 containing the E. coli st pre-pro sequence fused with the insulin chain B coding sequence in frame.

24. An E. coli host containing a vector or construct according to preceding clauses.

25. A process for the production of a protein heterologous to E. coli, by growing an E. coli host as defined in clause 24 and isolating the expressed protein.

26. A process according to clause 25 wherein the protein is secreted extracellularly.

27. A process according to clauses 25 and 26 wherein Angiotensin I is isolated.

28. A process according to clauses 25 or 26 wherein insulin chain A is isolated.

29. A process according to clauses 25 or 26 wherein insulin chain B is isolated.

30. A process for facilitating the secretion from the host cell of a protein expressed in a host cell which comprises fusing in reading frame DNA encoding the protein to be expressed to an E. coli st pre-pro sequence as defined in any one of clauses 1 to 11.

31. A process for forming a construct which comprises fusing a desired sequence at the Eco RI site of the pARC 0801 construct.

BRIEF DESCRIPTION OF THE DRAWINGS

FIG. 1: Sequence of st gene

DETAILED DESCRIPTION OF THE INVENTION

Figure 2:
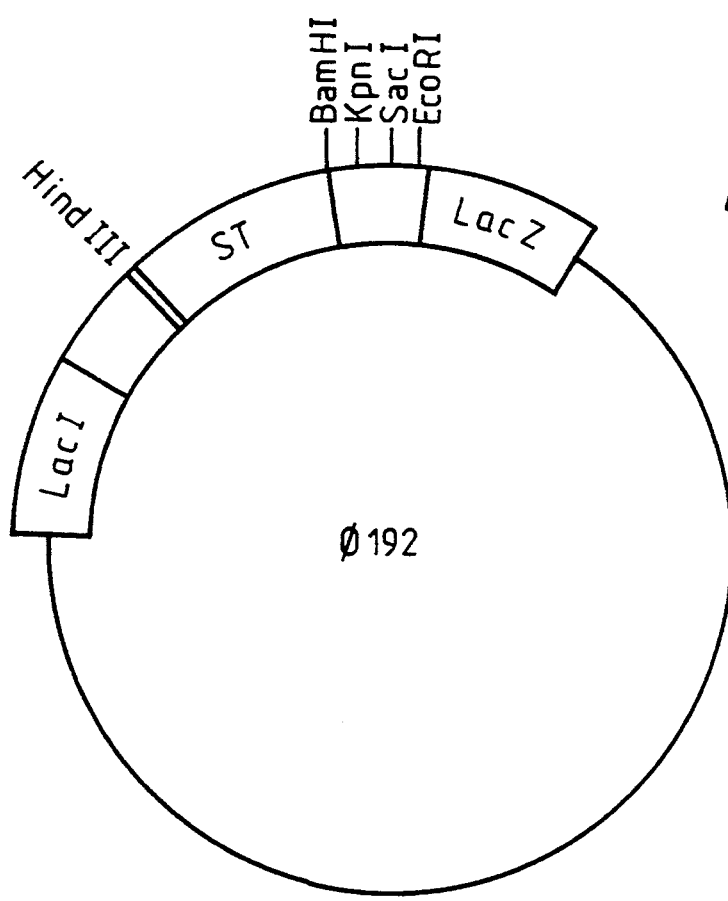
FIG. 2: Restriction map of φ192 construct (BamHi-HindIII fragments of st gene cloned into M13 mp19—BamHI HindIII site)

Identification and cloning of the human variety of E. coli stI gene was described in detail by P. Dwarakanath et al (1989, Gene, 81, 219–226). In brief, a plasmid of ca. 100 MDa was identified in E. coli strain 86 cal which contained the st gene. A BamHI library of the 100 MDa plasmid of E. coli 86 cal was constructed in pBR 322 and a st gene containing clone was identified by DNA probe hybridization. This st gene was further subcloned in M13mp19 as a BamHI - HindIII fragment and the complete fragment was sequenced by Sanger's method.

A part of the sequence containing the open reading frame (ORF) of the st gene is shown in FIG. 1. The carboxy terminal 19 aa of the ORF coded peptide corresponds to the sequence of the ST$_h$ peptide (Aimoto et al 1982 Eur. J. Biochem. 129, 257–263). Four nucleotides preceding the start codon, a sequence suggesting a putative ribosome binding site can be identified. The coding sequence is followed by a pair of stop codon (TAA) and a 15 nucleotide stretch with dyad symmetry presumably indicating a transcription termination signal. The ORF codes for a 72 amino acid peptide in which the 19 amino acid carboxy terminal is the biologically active peptide.

The 19 or 20 amino acid stretch at the N-terminus constitutes the signal peptide, having two basic residues [Lys2, Lys3] following the initiator methionine, a hydrophobic stretch of amino acids and a consensus sequence for signal cleavage junction. The exact cleavage junction of the signal peptide from the pro-ST region is not known. The pro ST region spans upto Met 53 where it is finally cleaved to yield a biologically active peptide secreted extracellularly with Asn54 as the N-terminal of the mature peptide.

Estimation of the $ST_h$ concentration culture supernatants was obtained using the competitive ELISA technique. This ELISA was routinely used throughout this investigation to estimate the level of $ST_h$ in culture supernatant. Hyperexpression of the st gene was achieved by subcloning the gene fragment in T7 promoter containing vector. In such a hyperexpression system the induction of hyperexpression was achieved by the addition of the inducer (isopropylthiogalactoside) IPTG. Purification scheme for the ST peptide (wild type/mutant) was according to the method described by P. Dwarakanath et al. (1989; Gene 81 219-226). Amino acid sequence analysis of the peptide was done by an Applied Biosystem Amino Acid Sequence Analyser (Model 477A). The in vitro site directed mutagenesis method was used to generate mutants in the pro region as well as in the mature part of the toxin peptide coding sequence following standards methods (Das et al 1989, Proc. Natl. Acad. Sci. U.S.A. 86, 496–499). Similarly, by in vibro site directed mutagenesis method the complete mature ST peptide coding region was replaced by Angiotensin I (Ang I) coding sequence and secretion of the Ang I was monitored by radioimmuno assay (RIA). The results are described under Experimental Data Section.

EXPERIMENTAL DATA

I. Construction of Secretion Vectors $ST_h$ was detected in the culture supernatant of an ETEC E. coli isolate 86 cal which was shown to harbor a plasmid of 100 MDa. A BamHI library of the 100 MDa plasmid of E. coli 86 cal was constructed in pBR 322 and the recombinant clones were checked for st gene. One of the recombinant clones was identified as carrying the st gene in a 1.9 Kb BamHI fragment (pARC 074). A 1.1 Kb BamHI - HindIII fragment obtained from pARC 074 was cloned in pBR 322 to obtain plasmid pARC 0101. The plasmid pARC 0101 is the starting material for all further experiments. This plasmid is deposited in National Collection of Industrial Bacteria, Aberdeen, Scotland (strain NCIB 40115), under the Budapest Treaty, the deposit date being Feb. 15, 1989. Culture supernatants of E. coli HB 101 harboring pARC 0101 elicit a positive biological response in suckling mice for ST.

II. Construction of M13mp19ss DNA Phage Containing St Insert

A 1.1 Kb BamHI - HindIII fragment containing st gene was isolated from pARC0101. This was subcloned in a M13mp19RF digested with BamHI and HindIII. The recombinant replicative form (RF) was transformed in JM101 and plated in presence of X-Gal and IPTG. The transformant white plagues were screened for st gene and one such phage clone was identified as φ192 (FIG. 2) which when propagated in JM101 releases stable toxin in the culture supernatant. φ192 is the starting material for all the in vitro mutagenesis experiments described.

Figure 3:
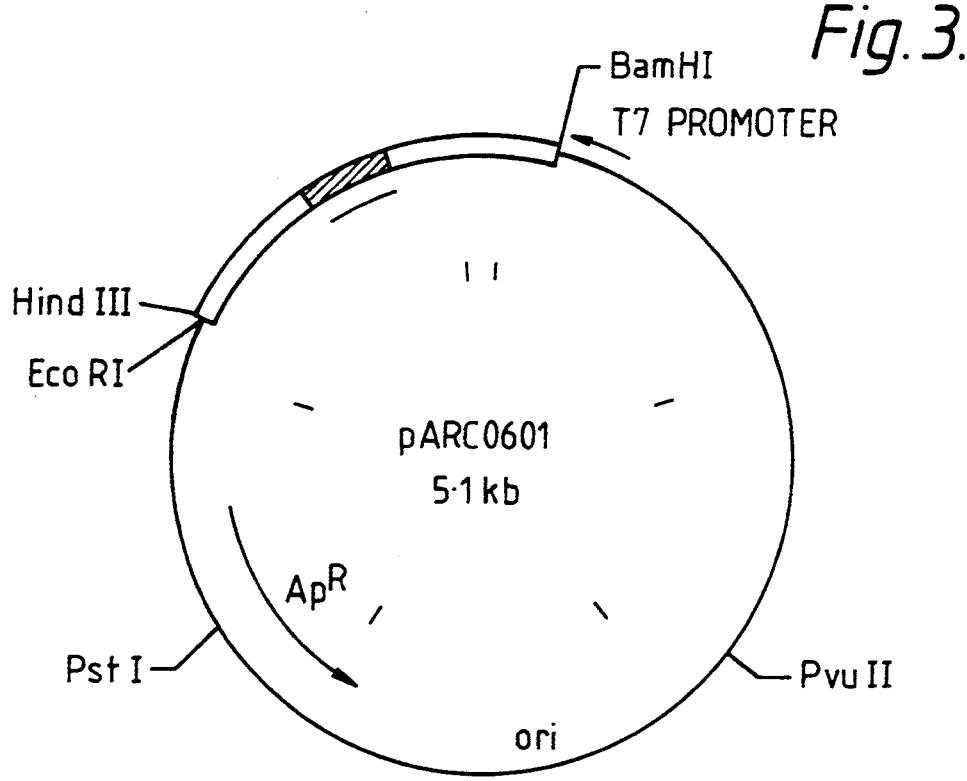
FIG. 3: st gene cloned into pET7 vector (BamHI HindIII site)

III. Construction of the Hyperexpression Vector for Hyperexpression of the Wild Type or Mutant $ST_h$ φ192 or its mutants were propagated in JM101 and the RF was isolated following an overnight growth of the bacteria following a standard protocol of plasmid purification [T. Maniatis et al. 1982 Molecular Cloning. A Laboratory Manual. Cold Spring Harbour Laboratory, Code Spring Harbour, N.Y.]. A BamHI-HindIII fragment of 1.1 Kb was isolated and subcloned in a T7 promoter containing vector as a BamHI-HindIII fragment such that the promoter was oriented in the same direction as that of the transcription of the st gene. The hyperexpression plasmid containing the wild type st gene was designated as pARC 0601 (FIG. 3).

IV. Examples to Demonstrate the Essentiality of the Pro Region for Extra Cellular Secretion To demonstrate the essentiality of the pro region for extracellular secretion of stable toxin, two mutants of the st gene were made where the mutation was located in the pro region. In the first example a mutation was made at the processing site where the Met53 was altered to Ile 53 using φ192 grown in CJ236 (dut⁻ ung⁻] strain as the template. The mutagenic primer used for creating this alteration had the sequence 5' C C T G A A A G C A T T A A T A G T A G C 3' (ATG→ATT). This primer (GD21) was annealed to the template and extended in the presence of Sequenase and the four dNTPs. The extended chain was ligated by T4 DNA ligase and this in vitro synthesized double stranded DNA was used to transform JM101. The transformant plaques were screened by DNA sequencing and the mutant clones were identified. One such mutant clone (φGD21) was plague purified and subcloned into the hyperexpression vector by the method as outlined in experimental data Section III. The resulting plasmid pARC 0701 was used to transform E. coli HB101. Production of extra cellular ST (M53→I53) in an overnight culture was compared with that of pARC 0601 grown in E. coli HB101. The result is shown below:

| Plasmid in HB101 | ST production in ug/ml |
| --- | --- |
| pARC0601 | 7 |
| pARC0701 | 1 |

This experiment showed that a conservative change (Met53→Ile53) in the pro region reduced the level of secretion of stable toxin by more than 85%.

The attenuation of $ST_h$ secretion was more evident when a deletion mutant of st was constructed where the deletion spanned from Ser48 to Ser52 in the pro region. Experimental protocol was the same as that described in the previous section except for the mutangenic primer used which had the sequence 5' G C A A A A A A A G T A A T A A A A T G A A T A G T A G C A A T T A C 3' (GD-11). Hyperexpression plasmid containing this mutant st (Del. Ser. 48- Ser52) was designated pARC 0702. When this plasmid was propagated in HB101, the resultant clone did not produce any detectable extracellular $ST_h$. These examples (Met53→Ile53 and Del. Ser48→Ser52) therefore clearly showed that the presence of intact pro region was necessary for extra cellular $ST_h$ secretion.

Figure 4:
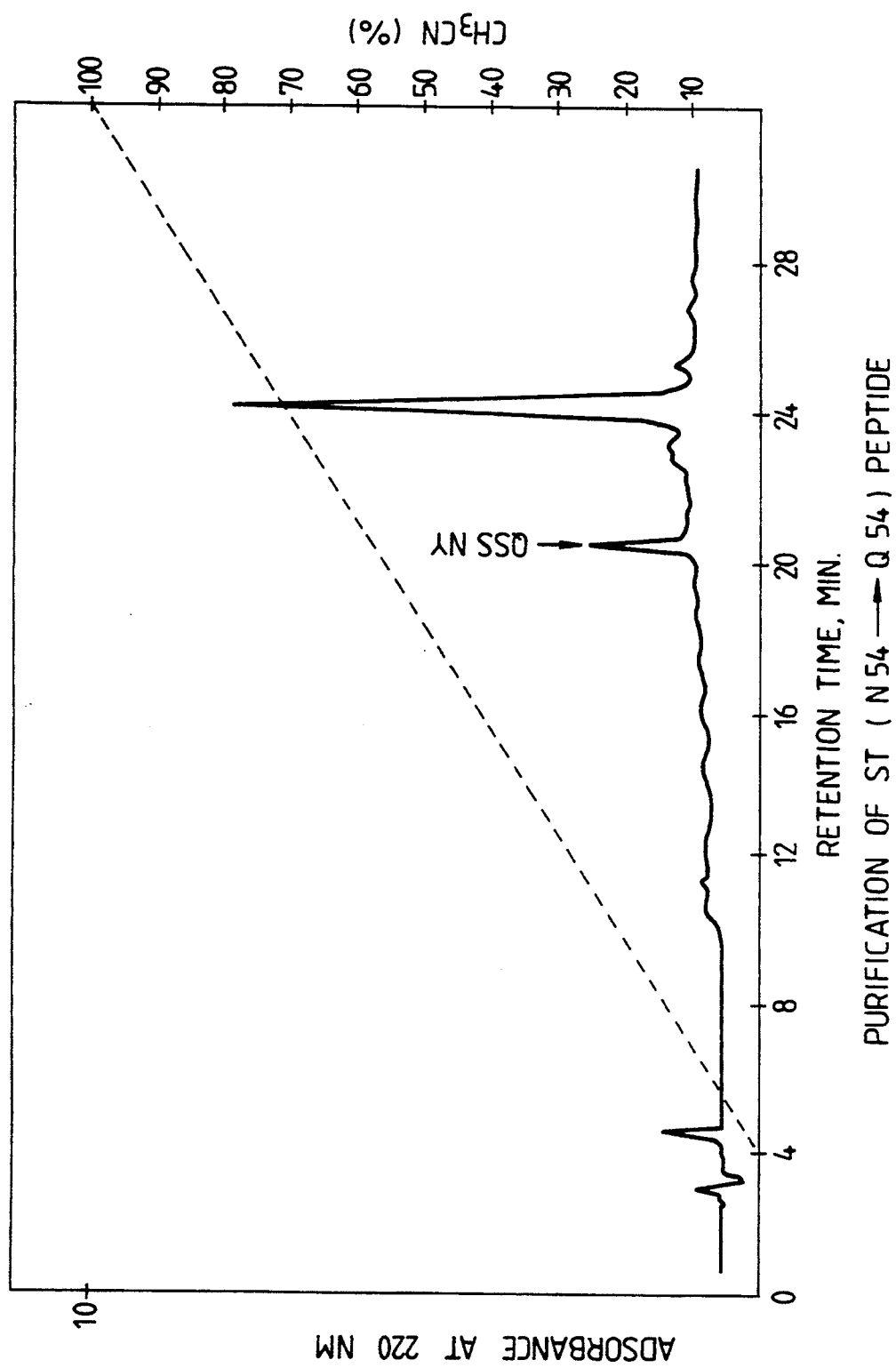
FIG. 4: Purification of st (N54-Q54) peptide. N-terminal sequence of the peak fraction indicated by single letter code.

V. Examples Demonstrating Non-specificity of the N-terminus Residue of the Mature Peptide for Correct Processing and Extra Cellular Secretion of the ST$_h$ Peptide To find the effect of the N-terminal residue of the ST peptide on the processing and extracellular secretion of the peptide two mutants of the st were made. In the first example, Asn54 of the STh was changed to Gln54 exactly following the method as described section III of Experimental Data. The mutagenic primer had the sequence of 5' G A A A G C A T G C A G A G T A G C A A T 3'(ATT→CAG). The hyperexpression plasmid containing the mutant st Asn54→Gln54 was designated pARC 0732. This plasmid when propagated in E. coli HB101 or in the hyperexpression strain BL21-DE3 produced equivalent amount of extracellular toxin compared to that produced by strains HB101 or BL21-DE3 harboring pARC 0601. In order to determine the processing site of the extracellularly secreted mutant ST (Asn54→Gln54), the mutant gene was overexpressed and the peptide was purified essentially following the method described by P. Dwarakanath et al (1989, Gene 81, 219-226). The HPLC purification profile is shown in FIG. 4. The N-terminal sequence of this peptide revealed a sequence Gln - Ser - Ser - Asn - Tyr.

Figure 5:
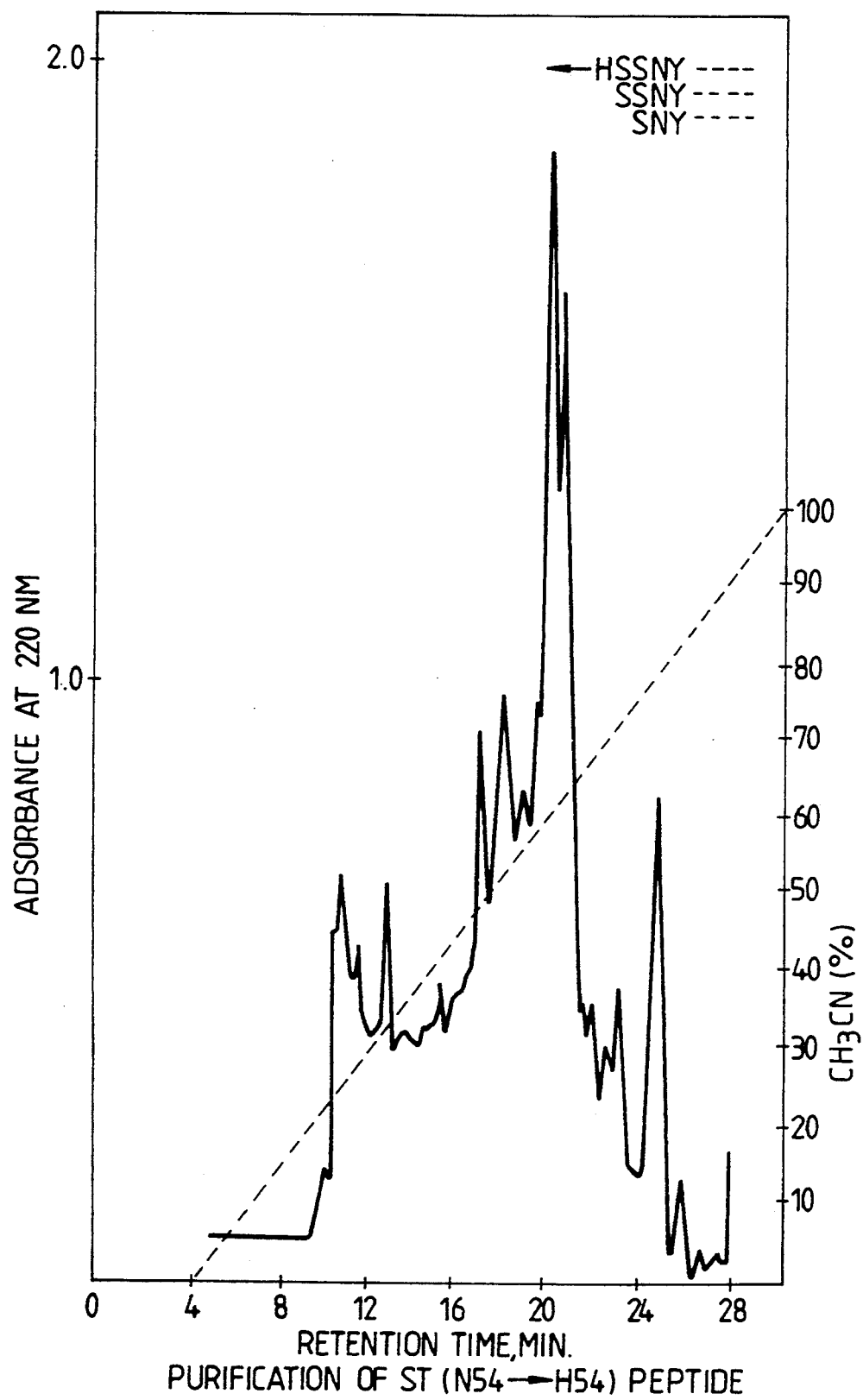
FIG. 5: Purification of st (N54-H54) peptide. N-terminal sequence of the peak fraction indicated by single letter code.

Another similar experiment was conducted in which Asn54 of STh was altered to His54. The resulting plasmid containing the mutant st was designated pARC 0716. Following overexpression of the st Asn54→Ile54 and purification of peptide, the N-terminal sequence of the peptide was determined. The sequence data showed presence of two peptides with N-terminal sequences (1) His-Ser-Ser-Asn-Tyr... and (2) Ser-Ser-Asn-Tyr... A HPLC purification profile of this peptide is shown in FIG. 5.

These examples clearly demonstrate that the N-terminus of the ST$_h$ peptide (Asn54) is not crucial for post translational processing and secretion of the peptide.

VI. Example to Demonstrate Generality of the Stable Toxin Based Secretion Vector To test the generality of the st based secretion vector, the coding region corresponding to mature ST peptide (i.e. Asn54 to Try72) was replaced in the st gene by Angiotensin I coding sequence. Angiotensin I is a decamer peptide which is converted from a larger precursor Angiotensinogen by Renin protease. Angiotensin I is further modified to yield Angiotensin II by 'Angiotensin converting enzyme' which deletes the last two carboxyl terminal residues (His-Leu) of Angiotensin I, Angiotensin II is known to be a potential vaso constrictor. The substitution of AngI coding sequence in place of ST coding sequence in the st gene was accomplished by Kunkel's method (T. A. Kunkel, 1985 Proc. Natl. Acad. Sci. USA 82, 488-492) with some modifications. A mutagenic primer (GD9) was synthesized having the sequence 5' G T G G T C C T G A A A G C A T G G A C C G G G T G T A C A T A C A C C C T T C C A C C T C T T A A T A A T A T A A A G G G 3'. This 62 mer primer was annealed to ss 0192 DNA template grown in CJ 236. The temperature for annealing reaction was 55° C. The amount of template used was 3 ug per reaction while the primer used was 10 ng. Following annealing, the extension reaction was carried out at 37° C. for 4 hrs in the presence of 8 units of Sequenase and four dNTPs (final conc. of each dNTP was 1 mM). The extension mix also contained 4 units of T4 DNA ligase for the ligation of the extended primer to take place. This complex was used to transform E. coli JM101 and the putative clones were identified by DNA sequencing. The Ang I coding sequence linked st was subcloned into the hyperexpression plasmid and the plasmid was designated as pARC 0726. This plasmid when propagated into HB101 or hyperexpression strain BL21-DE3, the plasmid bearing strains produced AngI peptide extra cellularly as detected by RIA. Following hyperexpression of pARC 0726 in BL21-DE3 in M9 medium the peptide was purified for N-terminal sequencing. The purification scheme is described below. We believe this purification scheme can be applied generally for other peptides.

Figure 6:
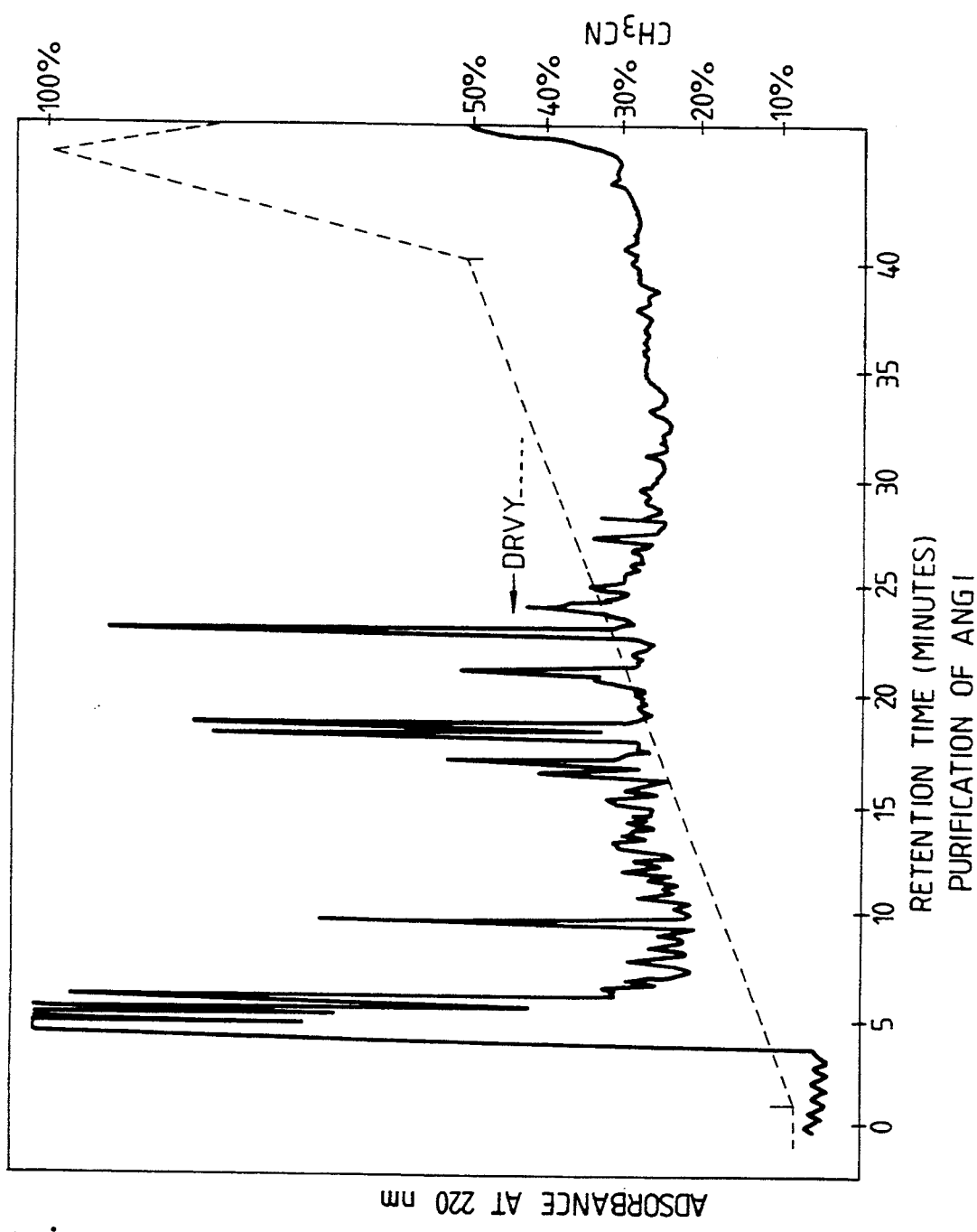
FIG. 6: Purification of Angiotensin I for pARC 0726.

BL21-DE3 cells harboring pARC 0726 were grown in M9 medium (250 m×4). When the culture reached an A600 nm=0.86, the cells were induced by adding IPTG (final conc. 0.5 mm). After 2.5 hrs following induction, cells were harvested and 470 ml of culture supernatant was mixed with 30 g of Amberlite XAD-4 and allowed to stand at room temperature overnight. After washing the resin thoroughly with water, the bound peptide was eluted with 99% Ethanol/1% acetic acid followed by 80% Ethanol/1% acetic acid. The eluate was concentrated by flash evaporation and the concentrate was loaded on SP Sephadex C-25 column (10 ml) previously equilibrated with 20 mM phosphate buffer, pH 6.4. Prior to elution, the column was rinsed with water. Elution was carried out with 50 mM triethylamine. The pH of the eluate was brought to 6.0 with acetic acid. The eluate was lyophilised and the dry powder was reconstituted in 1 ml water. The preparation was subject to HPLC on RP-8 column using an acetonitrile gradient [Solvent A:0.1% TFA, Solvent B:0.1% TFA/95% Acetonitrile: Flow rate 1 ml/min. Gradient was 10-50% B in 40 mins]. The Ang I peak was detected at 29% B (FIG. 6). The purified peptide was sequenced and the sequence was confirmed with the native sequence.

This example clearly demonstrates that a completely heterologous peptide coding sequence can be linked with st pro region and the correctly processed peptide can be detected extracellularly following propagation of such construct in a suitable E. coli host.

VII. Construction of a General Secretion Vector with Suitable Cloning Site

Introduction of a suitable cloning site in the mature peptide coding region can be accomplished as follows:

To introduce a restriction site within or at very close proximity to the mature peptide coding region, the DNA stretch 5' A T G A A T A G T 3' representing the amino acid sequence from Met53 to Ser55 is chosen. By altering the nucleotide sequence of Ser55 codon (AGT) to the alternate codon TCT, an EcoRI site could be generated without altering the amino acid residue. A schematic diagram is shown below:

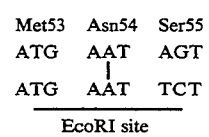

The single stranded (ss) φ192 DNA template is mutagenized by the method described earlier. The mutagenic primer (GD13) had a nucleotide sequence, 5'A G CATGAATTCTAGCAATTAC 3'. A general hyperexpression vector system can be constructed utilizing this EcoRI site as the suitable site for insertion of heterologous protein and peptide coding sequence. The hyperexpression plasmid pET7 is digested with EcoRI and BamHI and the large fragment isolated. φ192 (GD13) RF is isolated and digested with BamHI and EcoRI. Following CIP (calf intestinal phosphatase) treatment of the digestion product, a 620 bp fragment is isolated. This fragment is ligated with the large fragment of pET7. The resultant recombinant plasmid is named pARC 0801.

The plasmid pARC 0801 is deposited under the Budapest Treaty in the National Collection of Industrial and Marine Bacteria, Aberdeen, Scotland under no. NCIMB 40417. The date of deposit is Apr. 29, 1991.

Figure 7:
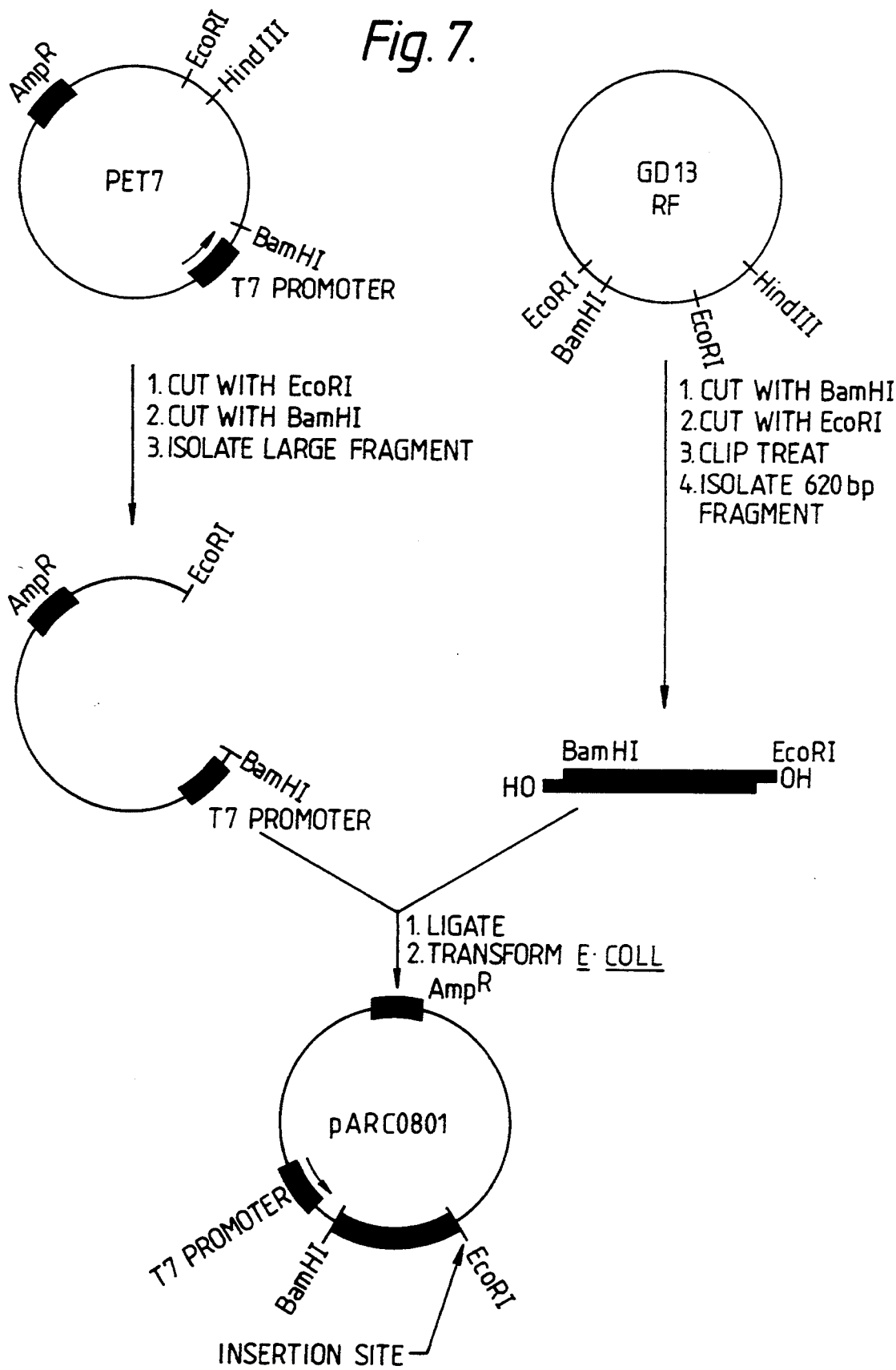
FIG. 7: Construction of pARC 0801 vector.

(FIG. 7) This plasmid can be used as a general secretion vector. Any heterologous peptide or protein coding sequence can be inserted at the EcoRI site (insertion site), for example, peptides such as Angiotensin I, bovine fibroblast growth factor, (bFGF), insulin, and others.

Expression of this plasmid in a E. coli, host, results in the secretion of the peptide or protein into the medium which can be purified. It should be noted that peptide produced from this recombinant plasmid will have one additional amino acid residue at its amino terminal (Ser).

The possibility of producing Angiotensin I and, especially, insulin, represent an important aspect of the present invention. Purified insulin A chain and insulin B chain can be used to produce insulin.

VIII. Examples to Demonstrate Secretion of Insulin A and B Chains from the Stable Toxin Base Secretion Vector The following example demonstrates the generality of the stable toxin based secretion vector. Human insulin consists of two polypeptide chains A (21 amino acid residues) and B (30 amino acid residues) which are linked through SH bonds. These chains can be separated in vitro by reduction and pure forms of A and B chains can be obtained. Under appropriate conditions purified A and B chains can be reoxidised to form immunoreactive and biologically active human insulin. The gene sequences of human insulin A and B chains were fused separately at the end of the ST pre- pro sequence. The recombinant plasmid harboured in actively growing E. coli hosts, secreted into the culture medium substances which were immunoreactive against human insulin antibody. Incubation of the human insulin antibody with authentic insulin A and B chains inhibited in a competitive manner in respective cases where recombinant A and B chains were expected to be produced, indicating that the expected product was produced in each case. The recombinant plasmids were constructed using the strategy similar to that described in Experimental Data VI. A M13 mp 19 based recombinant phage DNA (φGD24) was used as the template for the first round of mutagenesis. φGD24 had a ST gene inserted as a BamHI-HindIII fragment in M13 mp 19 multiple cloning site. This particular ST insert had a missense mutation at the N-terminal residue of the mature toxin peptide replacing the Asn 54 by Gly 54. The mutagenic primer used for introducing the first round of mutagenesis had the nucleotide sequence.

5' CCTGAAAGCATGGGTATCGTGGAG
CAGTGCTGTACATCTATCTGCTCA
CTGTATTAATAATATAAA 3'

This mutagenesis yielded the phage φGD26 which had the DNA sequence corresponding to the N-terminal 1–14 residues of insulin A chain fused in frame with the ST pre-pro region. GD26 DNA was used as the template for the second round of mutagenesis. The mutagenic primer had the nucleotide sequence

5' TGCTCACTGTATCAGCTAGAGAAC
TACTGCAACTAATAATATAAA 3'

Following mutagenesis, GD28 was identified which had the complete A chain gene fused at the C terminal section of the ST pre-pro region. In summary, with 2 rounds of mutagenesis the complete nucleotide sequence of insulin A chain gene was fused in frame at the 3' end of ST pre-pro sequence and thereby completely replacing the mature toxin gene sequence. However, rest of the 3' end sequence of the ST gene was retained intact in the final construct. The recombinant phage GD28 was grown in JM101 and the RF was isolated. The RF was digested with BamHI-HindIII and the 1.1 Kb fragment was cloned into pET7 as a BamHI-HindIII fragment to yield pARC 0750. The hyperexpression E. coli strain BL21-DE3 was transformed with pARC0750. In a similar manner insulin B chain was also synthesised and fused at the 3' end of the ST pre-pro region. The initial template used was GD23 which had a ST insert N54F. The nucleotide sequence of the first mutagenesis primer was 5' GGTCCTGAAAGCATGTTTGTGAAT
CAGCATCTTTGCGGAAGTCATCTG
GTTGAGGCTCTTTATTAATAATAT
AAA 3'

Following mutagenesis a mutant clone was identified (φGD32) which had the DNA sequence corresponding to the insulin B chain 1–16 residues fused in frame with ST pre-pro sequence. φGD32 ss DNA was used as the template for the 2nd round of mutagenesis. The nucleotide sequence of the mutagenic primer was

5' GTTGAGGCTCTTTATCTTGTATGT
GGTGAACGTGGTTTCTTCTATACA
CCTAAGACATAATAATATAAAGGG
3'

Following mutagenesis, the mutant phage φGD33 was isolated which had the complete B chain gene sequence fused at the 3' end of the ST pre-pro sequence. This fused gene insert was isolated from φGD33 as the BamHI-HindIII fragment and subcloned in pET7 to yield pARC 0759. E. coli hyperexpression strain BL21-DE3 was transformed with pARC0759 and the transformed clones were screened for the presence of the plasmid. To check whether the clones pARC0750 and pARC0759 were secreting A and B chains respectively, ELISA procedures were developed where culture supernatants could be directly tested. Essential features of the ELISA procedure are described below:

Human insulin was purchased from Novo Industries. It was in a highly pure form which was confirmed on reverse phase HPLC analysis. An aliquot of this pure insulin was reduced quantitatively with DTT and carboxyamidated using iodoacetamide to form stable A & B chains. A direct ELISA as well as an inhibition ELISA for A & B chain detection were developed using antibody raised against human insulin. pARC0750 and pARC0759 in BL21-DE3 host were grown separately in M9 medium and induced with IPTG as described in the previous examples. Following induction the cultures were centrifuged and the supernatants were checked for the presence of A & B chains. The yield of A and B chains as estimated by direct ELISA were approximately 16 ug/ml and 30 ug/ml respectively. Inhibition ELISA studies also confirmed the quantitative estimation or the secretion level of the A & B chains respectively.

The matter contained in each of the following claims is to be read as part of the general description of the present invention.

I claim:

1. A vector capable of facilitating the extracellular secretion of heterologous protein expressed in a host cell, said vector including DNA encoding the *E. coli* st pre-pro sequence M K K S I L M I F L S V L S F S P F A Q D A K P V E S S K E K I T K E S K K C N I A K K S N K S G P E S M.

2. A vector according to claim 1 containing the BamHI-HindIII segment of the *E. coli* st pre-pro sequence as defined in claim 1.

3. The vector pARC 0101, Deposit No. NCIB 40115.

4. A construct comprising a vector selected from the group consisting of a vector capable of facilitating the secretion of heterologous protein expressed in a host cell, said vector including DNA encoding the *E. coli* st pre-pro sequence M K K S I L M I F L S V L S F S P F A O D A K P V E S S K E K I T K E S K K C N I A K K S N K S G P E S M; a vector containing the BamHI-HindIII segment of the *E. coli* st pre-pro sequence; and the vector pARC 0101, Deposit No. NCIB 40115 fused in reading frame to DNA encoding a desired protein.

5. A construct according to claim 4 wherein the DNA encodes Angiotensin I.

6. A construct according to claim 4 wherein the DNA encodes insulin A chain.

7. A construct according to claim 4 wherein the DNA encodes insulin B chain.

8. The construct pARC 0726 containing the *E. coli* st pre-pro sequence fused with the Angiotensin I coding sequence in frame.

9. The construct pARC 0750 containing the *E. coli* st pre-pro sequence fused with the insulin chain A coding sequence in frame.

10. The construct pARC 0750 containing the *E. coli* st pre-pro sequence fused with the insulin chain B coding sequence in frame.

11. An *E. coli* host containing a vector or construct according to any one of claims 1–10.

12. A process for facilitating the extracellular secretion from the host cell of a protein expressed in a host cell which comprises fusing in reading frame DNA encoding the protein to be expressed to an *E. coli* st pre-pro sequence according to any one of claims 1 to 10.

13. A process for the production of a protein heterologous to *E. coli* which comprises growing an *E. coli* host which contains a vector or construct capable of facilitating the secretion of heterologous proteins expressed in a host cell, said vector or construct including DNA which encodes the *E. coli* st pre-pro sequence M K K S I L M I F L S V L S F S P F A O D A K P V E S S K E K I T K E S K K C N I A K K S N K S G P E S M, and isolating the expressed protein.

14. A process according to claim 13 wherein the protein is secreted extracellularly.

15. A process according to claim 13 or 14 wherein Angiotensin I is isolated.

16. A process according to claim 13 or 14 wherein insulin chain A is isolated.

17. A process according to claim 13 or 14 wherein insulin chain B is isolated.

18. A process according to claim 15 wherein the vector contains the BamHI-HindIII segment of the *E. coli* st pre-pro sequence.

19. A process according to claim 16 wherein the vector contains the BamHI-HindIII segment of the *E. coli* st pre-pro sequence.

20. A process according to claim 17, wherein the vector contains the BamHI-HindIII segment of the *E. coli* st pre-pro sequence.

21. A process according to claim 15 wherein the vector is pARC 0101, Deposit No. NCIB 40115.

22. A process according to claim 16 wherein the vector is pARC 0101, Deposit No. NCIB 40115.

23. A process according to claim 17 wherein the vector is pARC 0101, Deposit No. NCIB 40115.

24. A process for forming a construct which comprises ligating a desired sequence at the Eco RI site of the pARC 0801 construct.

25. The construct pARC 0801, deposit no. NCIMB 40417.

26. A method employing an expression vector for production and extracellular secretion of a heterologous protein which comprises:
  (a) ligating a coding sequence of the heterologous protein in frame to the 3' terminus of the *E. coli* st I pre-pro sequence coding for M K K S I L M I F L S V L S F S P F A Q D A K P V E S S K E K I T K E S K K C N I A K K S N K S G P E S M, wherein the 5' terminus of the *E. coli* st I pre-pro sequence is ligated to a heterologous or homologous promoter in an expression vector;
  (b) infecting an appropriate host cell with the expression vector for secretion of a heterologous protein;
  (c) growing the host cell harboring the expression vector in a medium suitable for expression; and
  (d) isolating the heterologous protein from the medium.

27. The method of claim 26 wherein the vector is pARC 0101, Deposit No. NCIB 40115.

28. A method for the expression of Angiotensin I which comprises ligating the construct pARC 0726 containing the *E. coli* st pre-pro coding sequence with the Angiotensin I coding sequence in frame, introducing the resultant recombinant DNA into an appropriate cell line and expressing Angiotensin I.

29. A method for the expression of insulin chain A which comprises ligating the construct pARC 0726 containing the *E. coli* st pre-pro coding sequence to the insulin chain A coding sequence in frame, introducing the resultant recombinant DNA into an appropriate cell line and expressing insulin chain A.

30. A method for the expression of insulin chain B which comprises ligating the construct pARC 0726 containing the *E. coli* st pre-pro coding sequence to the insulin chain B coding sequence in frame, introducing the resultant recombinant DNA into an appropriate cell line and expressing insulin chain B.

* * * * *